US008852102B2

(12) United States Patent  
Miyachi

(10) Patent No.: US 8,852,102 B2  
(45) Date of Patent: Oct. 7, 2014

(54) ULTRASOUND DIAGNOSTIC APPARATUS AND METHOD OF DETERMINING ELASTICITY INDEX RELIABILITY

(75) Inventor: Yukiya Miyachi, Ashigara-kami-gun (JP)

(73) Assignee: FUJIFILM Corporation, Tokyo (JP)

( * ) Notice: Subject to any disclaimer, the term of this patent is extended or adjusted under 35 U.S.C. 154(b) by 151 days.

(21) Appl. No.: 13/408,694

(22) Filed: Feb. 29, 2012

(65) Prior Publication Data

US 2012/0232387 A1 Sep. 13, 2012

(30) Foreign Application Priority Data

Mar. 8, 2011 (JP) ................................. 2011-050130

(51) Int. Cl.
*A61B 8/00* (2006.01)
*A61B 5/02* (2006.01)
*A61B 5/022* (2006.01)
*A61B 8/08* (2006.01)

(52) U.S. Cl.
CPC .................. *A61B 8/485* (2013.01); *A61B 5/022* (2013.01); *A61B 8/0858* (2013.01); *A61B 8/5276* (2013.01); *A61B 5/02007* (2013.01); *A61B 8/469* (2013.01); *A61B 8/5223* (2013.01); *A61B 8/0891* (2013.01)
USPC ............ 600/438; 600/437; 600/443; 600/449

(58) Field of Classification Search
USPC .......................................... 600/437, 443, 449
See application file for complete search history.

(56) References Cited

U.S. PATENT DOCUMENTS

| 5,840,028 | A | 11/1998 | Chubachi et al. | |
|---|---|---|---|---|
| 2005/0004467 | A1* | 1/2005 | Shiina et al. | 600/449 |
| 2008/0021318 | A1* | 1/2008 | Kato et al. | 600/437 |
| 2008/0081993 | A1* | 4/2008 | Waki | 600/438 |
| 2009/0012399 | A1 | 1/2009 | Sunagawa et al. | |
| 2009/0124901 | A1* | 5/2009 | Fink et al. | 600/437 |
| 2010/0081929 | A1* | 4/2010 | Suzuki | 600/437 |
| 2010/0113930 | A1 | 5/2010 | Miyachi | |
| 2010/0185090 | A1* | 7/2010 | Suzuki et al. | 600/443 |

FOREIGN PATENT DOCUMENTS

| JP | 10-5226 A | 1/1998 |
|---|---|---|
| JP | 2007-006914 | 1/2007 |
| JP | 2011-036271 | 2/2011 |

OTHER PUBLICATIONS

Extended European Search Report dated Jul. 6, 2012 in corresponding European Patent Application No. 12155563.5, 8 pages.
Notification of Reasons for Refusal, dated Jan. 29, 2013, issued in corresponding JP Application No. 2011-050130, 9 pages in English and Japanese.

* cited by examiner

*Primary Examiner* — Baisakhi Roy
(74) *Attorney, Agent, or Firm* — Sughrue Mion, PLLC

(57) ABSTRACT

An ultrasound diagnostic apparatus and a method of determining elasticity index reliability control transmission and reception of an ultrasonic beam, track displacements in a transmission direction of a plurality of points of a blood vessel in the transmission direction of the ultrasonic beam, calculate an elasticity index of the blood vessel based on the tracking result, acquire the direction of a displacement or the amount of displacement in the transmission direction of a specific point of the blood vessel, and determine reliability of the elasticity index based on the acquisition result. A program for determining elasticity index reliability causes a computer to execute the respective steps of the method. A computer readable storage medium stores the program.

9 Claims, 10 Drawing Sheets

FIG. 10

| | FROM ANTERIOR | | | WITH VEIN AS WINDOW | | | PRESS WITH VEIN AS WINDOW | | |
|---|---|---|---|---|---|---|---|---|---|
| | 1 | 2 | 3 | 1 | 2 | 3 | 1 | 2 | 3 |
| BLOOD VESSEL CENTER DISPLACEMENT (mm) IN 1 HEARTBEAT | 0.12 | 0.09 | 0.11 | 0.49 | 0.60 | 0.80 | 0.21 | 0.12 | 0.14 |
| DISPLACEMENT (mm) FROM MINIMUM DIAMETER TIMING TO MAXIMUM DIAMETER TIMING OF POSTERIOR VASCULAR WALL | −0.19 | −0.14 | −0.14 | 0.22 | 0.11 | 0.19 | −0.04 | −0.12 | −0.12 |
| DISPLACEMENT (mm) FROM MINIMUM DIAMETER TIMING TO MAXIMUM DIAMETER TIMING OF BLOOD VESSEL CENTER | −0.07 | −0.03 | −0.04 | 0.34 | 0.24 | 0.30 | 0.08 | −0.02 | −0.01 |
| RELIABILITY OF ELASTIC MODULUS | ○ | ○ | ○ | × | × | × | ○ | ○ | ○ |

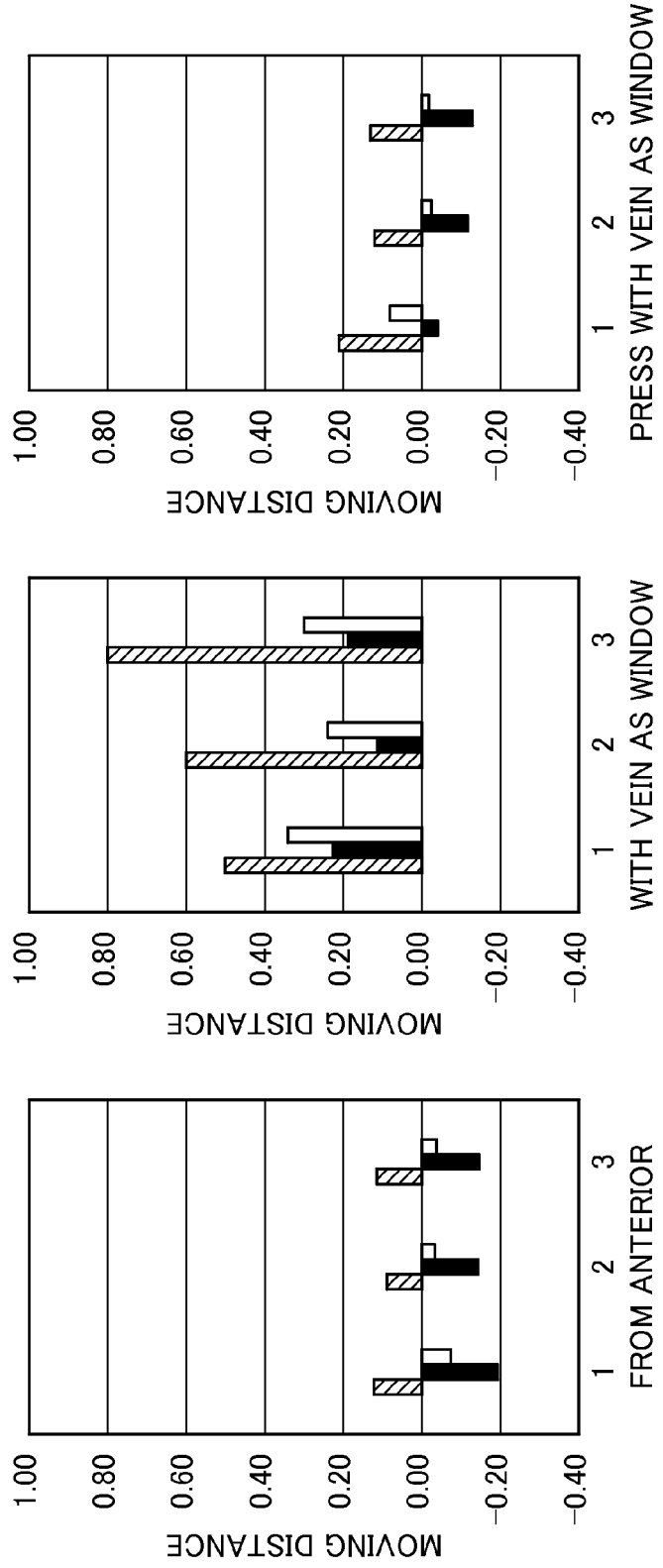

ULTRASOUND DIAGNOSTIC APPARATUS AND METHOD OF DETERMINING ELASTICITY INDEX RELIABILITY

BACKGROUND OF THE INVENTION

The present invention relates to a technique for measuring an elasticity index of a blood vessel using an ultrasonic wave, and evaluating and determining the reliability of the elasticity index. In particular, the present invention relates to an ultrasound diagnostic apparatus, a method of determining elasticity index reliability, and a program for determining elasticity index reliability which determine the reliability of an elasticity index of a blood vessel obtained by measurement using an ultrasonic wave.

In order to perform non-invasive cardiac diagnosis on the basis of acoustic and elastic characteristics of the heart muscle, it is necessary to percutaneously measure microvibrations having an amplitude equal to several tens of μm or less in each site of a heart wall over a frequency band up to hundreds of Hz consecutively over several beats. Accordingly, a technique is known in which the instantaneous position of a vascular wall is determined using the amplitude and phase of a detected signal, and the large amplitude displacement motion of the vascular wall based on a heart stroke is tracked, thereby obtaining the elastic modulus of a blood vessel (see JP 10-5226 A). Specifically, the motion rate waveform of microvibrations of a vascular wall is obtained on the basis of the sequential position of the vascular wall, tracking loci of parts taken at predetermined intervals in the depth direction of the vascular wall are obtained, and temporal changes in thickness of the parts are calculated, thereby obtaining the elastic modulus of a blood vessel.

SUMMARY OF THE INVENTION

However, when measuring the elastic modulus of the blood vessel, it is necessary to track the displacement of a vascular wall which is constantly in motion due to heartbeat. Meanwhile, it can be understood that, if the displacement due to heartbeat is excessive or if the position of the blood vessel to be measured is shifted, tracking fails, and the reliability of the obtained elastic modulus is deteriorated.

The invention has been finalized in consideration of the above-described situation, and an object of the invention is to provide an ultrasound diagnostic apparatus, a method of determining elasticity index reliability, and a program for determining elasticity index reliability capable of evaluating and determining the reliability of an elasticity index, such as an elastic modulus, measured using an ultrasonic wave, giving notification to a user, such as a measurement technician, when reliability is lacking, and preventing various diagnoses from being performed on the basis of an elasticity index, such as an unreliable elastic modulus, thereby performing accurate diagnosis.

In order to achieve the above objects, the present invention provides an ultrasound diagnostic apparatus comprising: control means for controlling transmission and reception of an ultrasonic beam; tracking means for tracking displacements in a transmission direction of a plurality of points of a blood vessel in the transmission direction of the ultrasonic beam; calculation means for calculating an elasticity index of the blood vessel based on the tracking result of the tracking means; acquisition means for acquiring the direction of a displacement or the amount of displacement in the transmission direction of a specific point of the blood vessel; and determination means for determining reliability of the elasticity index based on the acquisition result of the acquisition means.

Preferably, the plurality of points are on a posterior vascular wall, and the specific point is at least on the posterior vascular wall.

When the posterior vascular wall is displaced toward outside of the blood vessel in a heart contraction phase, the determination means preferably determines that the reliability of the elasticity index is high.

When the posterior vascular wall is displaced toward an anterior vascular wall by equal to or greater than 0.11 mm during a period in which the blood vessel increases from a minimum diameter to a maximum diameter, the determination means preferably determines that the reliability of the elasticity index is low.

Preferably, the plurality of points are on a posterior vascular wall, and the specific point is on an anterior vascular wall and the posterior vascular wall.

When the center position of the blood vessel is displaced toward the anterior wall by equal to or greater than 0.24 mm during a period in which the blood vessel increases from a minimum diameter to a maximum diameter, the determination means preferably determines that the reliability of the elasticity index is low.

When a blood vessel center displacement toward the anterior wall in one heartbeat is equal to or greater than 0.49 mm, the determination means preferably determines that the reliability of the elasticity index is low.

Preferably, the ultrasound diagnostic apparatus further comprises warning means for giving a warning when the determination means determines that the reliability of the elasticity index is low.

The blood vessel is preferably a carotid artery of a human body.

The present invention also provides a method of determining elasticity index reliability, the method comprising: a control step of controlling transmission and reception of an ultrasonic beam; a tracking step of tracking displacements in a transmission direction of a plurality of points of a blood vessel in the transmission direction of the ultrasonic beam; a calculation step of calculating an elasticity index of the blood vessel based on the tracking result in the tracking step; an acquisition step of acquiring the direction of a displacement or the amount of displacement in the transmission direction of a specific point of the blood vessel; and a determination step of determining the reliability of the elasticity index based on the acquisition result in the acquisition step.

The present invention also provides a program for determining elasticity index reliability, the program causing a computer to execute the control step, the tracking step, the calculation step, the acquisition step, the blood vessel and the determination step of the method of determining elasticity index reliability.

The present invention also provides a computer readable storage medium with the program for determining elasticity index reliability stored therein.

According to the invention, it is possible to evaluate and determine the reliability of an elastic modulus measured using an ultrasonic wave, give notification to a user, such as a measurement technician, when reliability is lacking, and prevent the user from continuing to make unnecessary measurement without change or making various diagnoses on the basis of an elastic modulus lacking in reliability, thereby performing accurate diagnosis.

BRIEF DESCRIPTION OF THE DRAWINGS

FIG. 10 is a table showing a blood vessel center displacement in one heartbeat, displacements from a minimum diameter timing to a maximum diameter timing of a posterior vascular wall and a blood vessel center, and the reliability of an elastic modulus when measured from different directions.

FIGS. 13A, 13B, and 13C are graphs showing a change of each part of a blood vessel in one heartbeat when measured from different directions with the jugular vein as a window while an ultrasound probe is pushed and abutted on a subject.

DETAILED DESCRIPTION OF THE INVENTION

Figure 1:
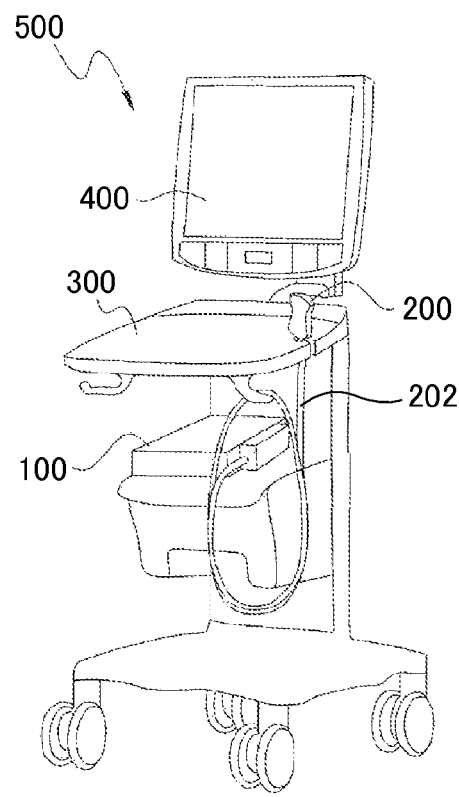
FIG. 1 is a perspective view showing the appearance of the main configuration of an ultrasound diagnostic system according to Embodiment 1 of the invention.

Hereinafter, embodiments of the invention will be described with reference to the accompanying drawings. The same components are denoted by the same reference numerals.

Embodiment 1

FIG. 1 is a perspective view showing an example of the appearance of the main configuration of an ultrasound diagnostic system 500 according to Embodiment 1 of the invention. Here, description will be provided as to a case where an ultrasound probe serving as a probe, an ultrasound diagnostic apparatus which controls the ultrasound probe, analyzes the reception signal of an obtained ultrasonic echo and synthesizes an image, and a display which displays the synthesized image are separately provided.

As shown in FIG. 1, the ultrasound diagnostic system 500 includes an ultrasound diagnostic apparatus 100, an ultrasound probe 200, a user operating unit 300, and a display 400.

Though not shown, the ultrasound probe 200 is a probe which performs transmission and reception of an ultrasonic beam by a plurality of ultrasound transducers of a one-dimensional or two-dimensional transducer array, and is used in a state where an array portion at the tip thereof having the ultrasound transducers arranged thereon abuts on the surface of a subject. The ultrasound transducers transmit an ultrasonic beam toward the subject in response to an actuation signal to be applied, receive an ultrasonic echo reflected by the subject, and output a reception signal. Each ultrasound transducer is constituted by a vibrator in which electrodes are formed at both ends of a piezoelectric material (piezoelectric body), such as piezoelectric ceramic represented by PZT (Pb (lead) zirconate titanate) or a piezoelectric polymer represented by PVDF (polyvinylidene difluoride). If a pulsed or continuous-wave voltage is applied across the electrodes of the vibrator, the piezoelectric body expands and contracts. With the expansion and contraction, pulsed or continuous ultrasonic waves are produced from the vibrators, and the ultrasonic waves are synthesized to form an ultrasonic beam. When receiving the propagating ultrasonic echo, the vibrators expand and contract, and electric signals are produced. The electric signals are output as the reception signal of the ultrasonic echo. As the type of the ultrasound probe, there are various types, such as a convex type, a linear scan type, and a sector scan type. The ultrasound probe 200 is connected to the ultrasound diagnostic apparatus 100 by a cable 202, and the operation thereof is controlled by the ultrasound diagnostic apparatus 100.

The ultrasound diagnostic apparatus 100 has a function of performing overall control of the operations of the respective units of the ultrasound diagnostic system 500. The ultrasound diagnostic apparatus 100 transmits and receives an ultrasonic beam through the ultrasound probe 200, or produces a tomographic image from the received ultrasonic echo and displays the tomographic image on the display 400. The ultrasound diagnostic apparatus 100 produces a B-mode image or an M-mode image as a tomographic image, and displays the produced image on the display 400 in real time. The ultrasound diagnostic apparatus 100 also has a function of displaying a thickness change waveform of a vascular wall or the like or a function of calculating and displaying an elasticity index (in this case, for example, an elastic modulus) of a tissue under observation. The detailed configuration of the ultrasound diagnostic apparatus 100 will be described below.

The user operating unit 300 includes a keyboard, a pointing device, and various buttons or dials. An operator (user), such as a physician or a technician, operates the ultrasound diagnostic system 500 using the user operating unit 300. For example, the operator designates various setting values relating to the operation mode of the ultrasound diagnostic system 500 according to a site under observation or changes the depth of the focus of the ultrasonic beam transmitted from the ultrasound probe 200 using the user operating unit 300. The operator designates a region of interest (hereinafter, abbreviated as ROI) using the user operating unit 300.

The display 400 is, for example, a raster scan-type LCD or the like, and displays an ultrasound image as a moving image or a still image on the basis of analog-converted image signals output from the ultrasound diagnostic apparatus 100.

Figure 2:
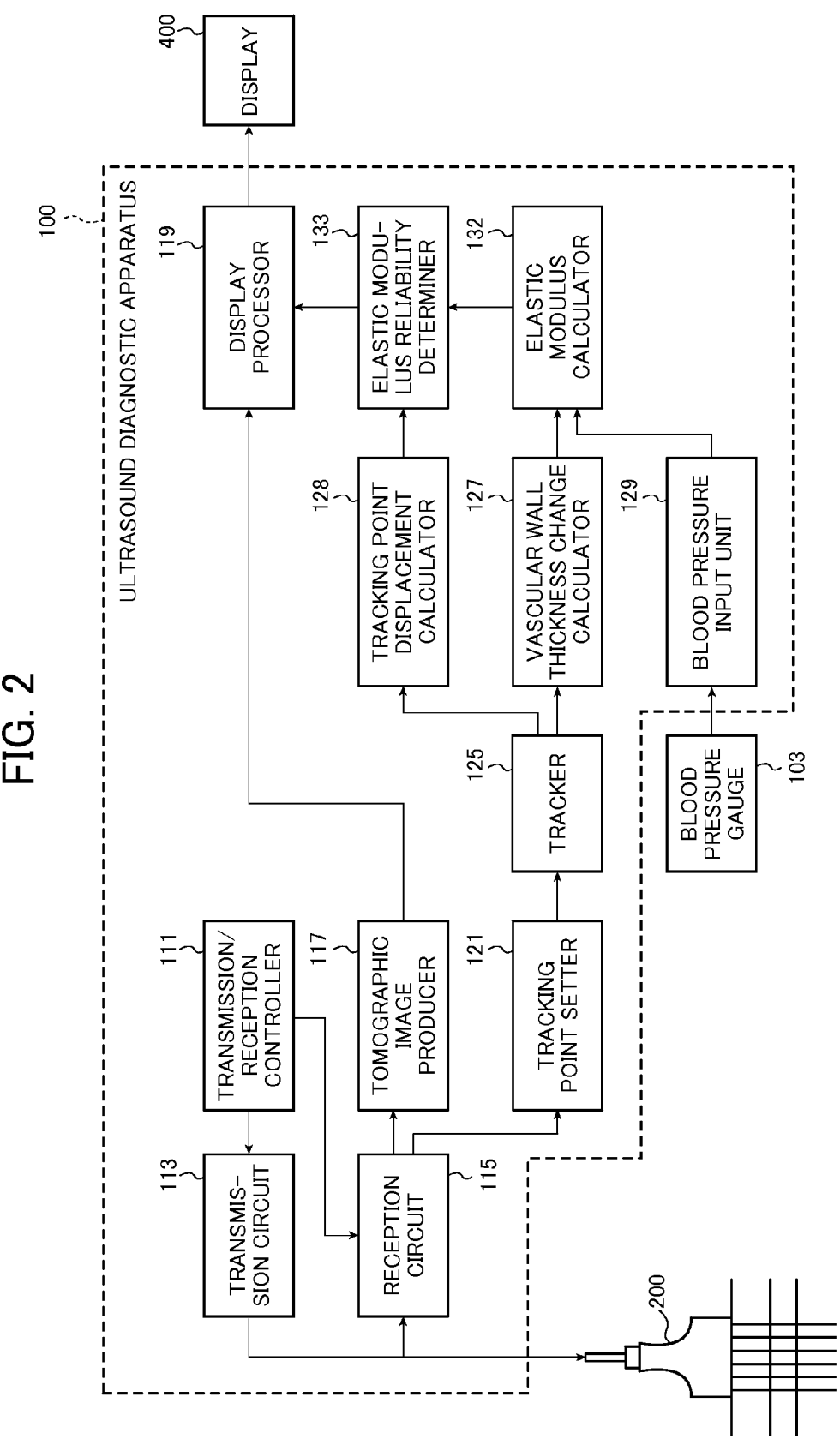
FIG. 2 is a block diagram showing the main configuration of an ultrasound diagnostic apparatus shown in FIG. 1 and peripheral devices connected to the ultrasound diagnostic apparatus.

FIG. 2 is a block diagram showing the main configuration of the ultrasound diagnostic apparatus 100 and peripheral devices connected to the ultrasound diagnostic apparatus 100.

Description of the configuration having already been shown in FIG. 1 will not be repeated.

The ultrasound diagnostic apparatus 100 includes a transmission/reception controller 111, a transmission circuit 113, a reception circuit 115, a tomographic image producer 117, a display processor 119, a tracking point setter 121, a tracker 125, a vascular wall thickness change calculator 127, a tracking point displacement calculator 128, a blood pressure input unit 129, an elastic modulus calculator 132, and an elastic modulus reliability determiner 133. As the peripheral devices connected to the ultrasound diagnostic apparatus 100, the ultrasound probe 200, a blood pressure gauge 103, and the display 400 are provided.

The transmission/reception controller 111 sequentially sets the transmission direction of the ultrasonic beam of the ultrasound probe 200 and the reception direction of the ultrasonic echo through the transmission circuit 113 and the reception circuit 115. The transmission/reception controller 111 has a transmission control function of selecting a transmission delay pattern in accordance with the set transmission direction and a reception control function of selecting a reception delay pattern in accordance with the set reception direction. The transmission delay pattern is the pattern of delay time which is imposed on the actuation signal of each ultrasound transducer so as to form an ultrasonic beam in a desired direction by ultrasonic waves transmitted from a plurality of ultrasound transducers of the ultrasound probe 200. The reception delay pattern is the pattern of delay time which is imposed on a reception signal so as to extract an ultrasonic echo from a desired direction by ultrasonic waves received by a plurality of ultrasound transducers. A plurality of transmission delay patterns and a plurality of reception delay patterns are stored in an internal memory (not shown), and are appropriately selected and used depending on the situation.

The transmission circuit 113 includes a plurality of channels, and produces a plurality of actuation signals which are applied to a plurality of ultrasound transducers of the ultrasound probe 200. At this time, the delay time can be imposed on each of a plurality of actuation signals on the basis of a transmission delay pattern selected by the transmission/reception controller 111. The transmission circuit 113 may adjust the delay amount of each of a plurality of actuation signals and supply a plurality of actuation signals to a plurality of ultrasound transducers of the ultrasound probe 200 such that ultrasonic waves transmitted from a plurality of ultrasound transducers form an ultrasonic beam. Alternatively, the transmission circuit 113 may supply a plurality of actuation signals to the ultrasound probe 200 such that ultrasonic waves transmitted from a plurality of ultrasound transducers at once reach the entire imaging region of the subject.

Similarly to the transmission circuit 113, the reception circuit 115 includes a plurality of channels. The reception circuit 115 amplifies a plurality of analog signals received through a plurality of ultrasound transducers, and converts the analog signals to digital reception signals. The reception circuit 115 performs a reception focus process in which the delay time is imposed on each of a plurality of reception signals on the basis of a reception delay pattern selected by the transmission/reception controller 111, and the reception signals are added. With this reception focus process, the focus of an ultrasonic echo is narrowed to form sound ray signals (sound ray data).

Next, the reception circuit 115 performs an envelope detection process on sound ray data through a low pass filter process or the like, and corrects attenuation depending on the distance in accordance with the depth of the reflection position of the ultrasonic wave through STC (Sensitivity Time gain Control). Sound ray data processed in the above-described manner is sequentially stored in a cine memory (not shown) which has storage capacity to accumulate sound ray data for a plurality of frames. The reception circuit 115 includes an image data producer (not shown). The reception circuit 115 directly inputs sound ray data to be directly supplied to the image data producer in a live mode, and inputs sound ray data to be supplied from the cine memory to the image data producer in a freeze mode. The reception circuit 115 performs a preprocess, such as Log (logarithmic) compression or gain adjustment, on sound ray data to produce image data, and outputs image data to the tomographic image producer 117 and the tracking point setter 121.

The tomographic image producer 117 converts (raster-converts) image data of an ultrasound image supplied from the reception circuit 115 to image data according to a normal television signal scan system, performs necessary image processes, such as a gradation process, and outputs image data to the display processor 119.

The tracking point setter 121 sets an ROI (region of interest) in an ultrasound image represented by image data supplied from the reception circuit 115, and sets a plurality of tracking points for automatic tracking of a vascular wall displacement waveform, a blood vessel diameter, or the like in the ROI in the depth direction (the transmission direction of the ultrasonic wave) of the subject. Information relating to the tracking points is output to the tracker 125. The operator may manually set the tracking points while viewing display on the display 400 or the tracking point setter 121 may automatically set the tracking points on the basis of a specific algorithm.

Although the tracking points set by the tracking point setter 121 are also used to determine the reliability of an elastic modulus described below, all the tracking points which are set for automatic tracking of a vascular wall displacement waveform, a blood vessel diameter, or the like may not be used to determine the reliability of an elastic modulus. Accordingly, the operator may manually set one or a plurality of specific tracking points, which are used to determine the reliability of an elastic modulus, from among all the tracking points, or the tracking point setter 121 may automatically set one or a plurality of tracking points, which are used to determine the reliability of an elastic modulus, on the basis of a specific algorithm.

Although in this embodiment, the setting of the ROI by the tracking point setter 121 is performed through operator's manual designation of the ROI by the user operating unit 300, the setting of the ROI may be automatically performed on the basis of image data. For example, in the case of ultrasound diagnosis of a carotid artery, since (1) an ultrasonic echo in a blood vessel is weak and low luminance is achieved on a B-mode image, and (2) in a cross-section where the carotid artery is viewed, the size of the carotid artery is about 1 cm and largest as a blood vessel, the carotid artery can be automatically detected comparatively simply from image data.

The tracker 125 automatically identifies each tracking point set by the tracking point setter 121 from ultrasonic tomographic image data, and recognizes the displacement of the tracking point as a tracking target, that is, a change in the position of a vascular wall (vascular wall displacement). The tracker 125 outputs a thickness change waveform of the vascular wall obtained by recognizing a change in the position of the vascular wall to the vascular wall thickness change calculator 127 as a vascular wall displacement waveform, and outputs the displacement of a specific tracking point for determining the reliability of an elastic modulus to the tracking point displacement calculator 128 as data. Displacement data output from the tracker 125 to the vascular wall thickness change calculator 127 may include only the displacement of the vascular posterior wall or may include both the displacement of the posterior wall and the displacement of the anterior wall.

The vascular wall thickness change calculator 127 obtains a heart contraction phase blood vessel diameter (maximum blood vessel diameter) Ds and a heart dilatation phase blood vessel diameter (minimum blood vessel diameter) Dd on the basis of the thickness change waveform of the vascular wall obtained by tracking in the tracker 125. That is, a change in the blood vessel diameter D is tracked from image data, and the maximum blood vessel diameter Ds and the minimum blood vessel diameter Dd are obtained. The vascular wall thickness change calculator 127 calculates a change in the thickness of the vascular wall from the thickness change waveform of the vascular wall and outputs the change in the thickness of the vascular wall to the elastic modulus calculator 132.

The tracking point displacement calculator 128 calculates the direction of the displacement and the amount of displacement in the depth direction (the transmission direction of the ultrasonic wave) of the subject at the specific tracking point from displacement data for determining the reliability of the elastic modulus supplied from the tracker 125, and outputs the direction of the displacement and the amount of displacement as the calculation result to the elastic modulus reliability determiner 133.

On the other hand, the blood pressure gauge 103 is a cuff-type blood pressure gauge in which a cuff is wound around the upper arm of the subject to measure a maximum value Ps and a minimum value Pd in correspondence with heart contraction and dilatation. Measured blood pressure data is automatically or manually input to the blood pressure input unit 129 of the ultrasound diagnostic apparatus 100.

The blood pressure input unit 129 is an interface with the blood pressure gauge 103 and the ultrasound diagnostic apparatus 100, and outputs input blood pressure data to the elastic modulus calculator 132.

The elastic modulus calculator 132 calculates an elastic modulus, which is one of the indexes representing blood vessel elasticity using vascular wall thickness change data and blood pressure data respectively supplied from the vascular wall thickness change calculator 127 and the blood pressure input unit 129, and outputs elastic modulus to the elastic modulus reliability determiner 133.

The elastic modulus reliability determiner 133 evaluates and determines the reliability of elastic modulus data supplied from the elastic modulus calculator 132 on the basis of the direction of the displacement and the amount of displacement output from the tracking point displacement calculator 128 by a process described below, and outputs the determination result to the display processor 119.

The display processor 119 generates image data for display on the basis of image data supplied from the tomographic image producer 117. The image for display is mainly a tomographic image, such as a B-mode image or an M-mode image, the thickness change waveform of the vascular wall, or the like, and the evaluation result or determination result supplied from the elastic modulus reliability determiner 133 is displayed together. When a notification signal indicating that the reliability of the elastic modulus is low is input from the elastic modulus reliability determiner 133, the display processor 119 displays a character, a figure, or the like on the display 400 to give a user a warning. The warning may be the sounding of an alarm tone, or the like. The display processor 119 may have an image processing function of performing an image process, such as a linear gradation process including gain adjustment and contrast adjustment or a nonlinear gradation process including γ correction. The display processor 119 includes a D/A converter, converts image data for display to an analog image signal, and outputs the analog image signal to the external display 400.

Figure 3:
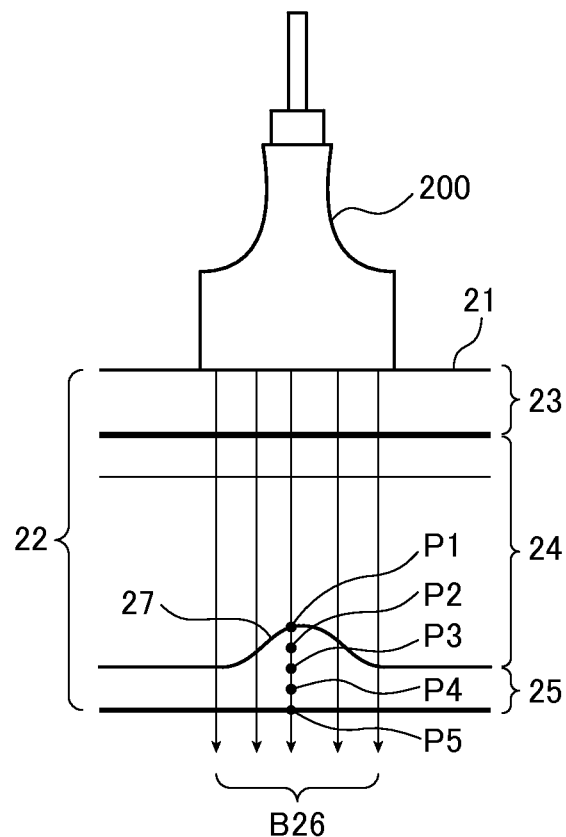
FIG. 3 is a schematic view illustrating the outline of a tracking process in the ultrasound diagnostic apparatus shown in FIG. 1.

FIG. 3 is a schematic view illustrating the outline of a tracking process which is performed on a vascular wall by the ultrasound diagnostic apparatus 100 of this embodiment.

As a method for the tracking process, there are various methods, such as a pattern matching method of a tomographic image, a zero cross point method, a tissue Doppler method, and a phase difference tracking method, and in principle, any method may be used. The ultrasound diagnostic apparatus 100 of this embodiment tracks the displacement in the position of each of a plurality of reflectors on an intima-media complex in a posterior vascular wall set on one ultrasonic beam using either or both of amplitude information and phase information of quadrature detection output.

For example, FIG. 3 shows an example where an ultrasonic beam B26 is transmitted from the ultrasound probe 200 toward a subject 21, the ultrasonic beam B26 passes through an anterior vascular wall 23 and an intravascular cavity 24 and reaches tracking points P1, P2, P3, P4, and P5 on a posterior vascular wall 25, the ultrasound diagnostic apparatus 100 receives an ultrasonic echo signal from each of the tracking points P1 to P5 through the ultrasound probe 200, and the tracker 125 tracks the vascular wall of a blood vessel 22, consequently, the thickness of the vascular wall. The tracking points P1 to P5 are manually or automatically set as the positions of five reflectors, that is, first to fifth reflectors (hereinafter, respectively called a reflector 1, a reflector 2, a reflector 3, a reflector 4, and a reflector 5) on the posterior vascular wall 25 by the tracking point setter 121. The tracker 125 tracks the set tracking points P1, P2, P3, P4, and P5, and obtains a temporal change in the position of each tracking point.

Although an example will be described where plaque 27 is on the posterior vascular wall 25, and a portion of the plaque 27 where part of the posterior vascular wall 25 is inflated toward the intravascular cavity 24 is tracked, as will be understood, the tracking process of the ultrasound diagnostic apparatus 100 may be performed even when no plaque is provided.

Figure 4:
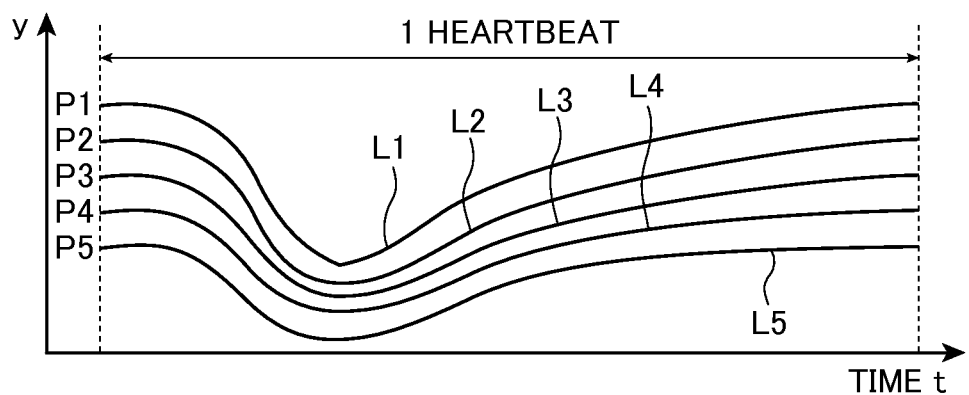
FIG. 4 is a graph showing an example of temporal changes in the positions y of tracking points P1 to P5.

FIG. 4 is a graph showing an example of temporal changes in the positions y of the tracking points P1 to P5 obtained by the tracker 125. Curves L1 to L5 which represent changes in the position correspond to the tracking points P1 to P5. From this drawing, it is obvious how the positions of the tracking points P1 to P5 are changed in a single heartbeat or whether or not there is a difference in the amount of displacement (the degree of recess) due to the tracking points. Accordingly, if the difference in the changes in the positions of adjacent reflectors (for example, P2 and P3) is calculated, the time-varying waveform of the vascular wall thickness can be obtained.

Figure 5A:
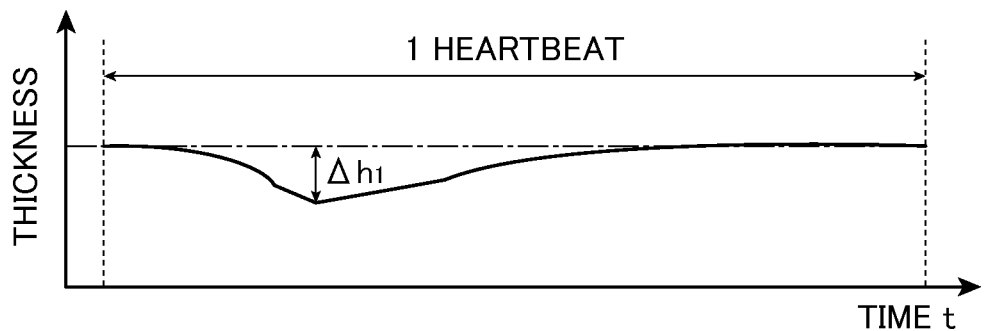
FIGS. 5A and 5B are graphs showing an example of a time-varying waveform of a thickness between adjacent reflectors.
Figure 5B:
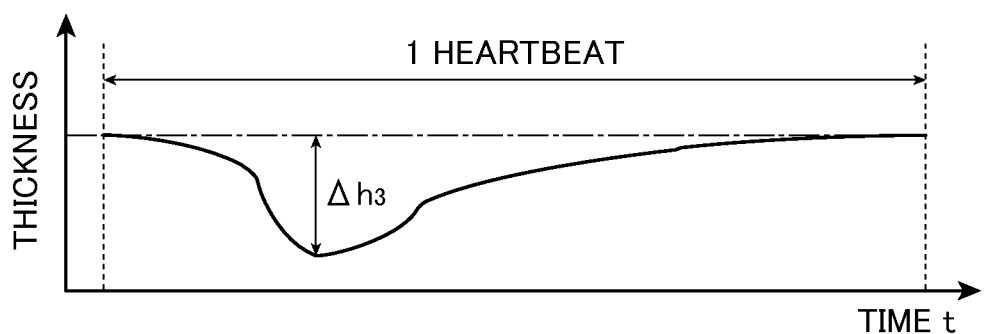

FIG. 5A shows a time-varying waveform of the thickness between the reflector 1 and the reflector 2 as adjacent reflectors of the vascular wall. In the drawing, Δh1 represents the amount of change in the thickness. FIG. 5B shows a time-varying waveform of a thickness between the reflector 3 and the reflector 4. In the drawing, Δh3 represents the amount of change in the thickness. From these drawings, it is understood that, while a tissue between the reflector 3 and the reflector 4 is a tissue which is comparatively soft and may be significantly recessed by pressure, a tissue between the reflector 1 and the reflector 2 is a tissue which is comparatively hard and cannot be significantly recessed due to pressure, that is, a hardened tissue.

As described above, although the degree of elasticity of the vascular wall can be recognized by the time-varying waveform of the vascular wall thickness, for more quantitative discussion, distortion ϵ of a blood vessel in the radial direction can be calculated by Expression (1).

$$\epsilon_i = \Delta h_i / h_{di} \quad (1)$$

Here, $\epsilon_i$ represents distortion in the radial direction between reflectors i and i+1 of the vascular wall, $\Delta h_i$ represents the maximum value of a change in the thickness between the reflectors i and i+1 in the heart contraction phase, and $h_{di}$ represents a thickness between the reflectors i and i+1 at the end of the heart dilatation phase.

In the elastic modulus calculator 132, an elastic modulus $E_{ri}$ in the radial direction and an elastic modulus $E_{\theta i}$ in the circumferential direction between the reflectors of the vascular wall can be calculated by Expressions (2) and (3) further using the blood pressure measured by the blood pressure gauge 103.

$$E_{ri} = \frac{\Delta p}{(\Delta h_i / h_{di})} \quad (2)$$

$$E_{\theta t} = \frac{1}{2}\left(\frac{r_d}{h_d} + 1\right) \cdot \frac{\Delta p}{(\Delta h_i / h_{di})} \quad (3)$$

Here, $r_d$ represents an intravascular radius at the end of the hear dilatation phase, $h_d$ is a vascular wall thickness at the end of the heart dilatation phase, $h_{di}$ is a thickness between the reflectors i and i+1 at the end of the heart dilatation phase, $\Delta h_i$ is the maximum value of a change in the thickness between the reflectors i and i+1 in the heart contraction phase, and $\Delta p$ represents a blood pressure difference between the heart contraction phase and the dilatation phase.

Although the elastic modulus of the vascular wall or the like is measured by the above-described method, the study of the inventors shows that, when tracking is measured by the above-described method, the measurement precision of the elastic modulus may be considerably lowered. This is presumably because the measurement of the elastic modulus is performed on the premise that a minute displacement of the vascular wall in motion can be correctly tracked. For example, it is understood that, when tracking of a minute displacement has failed due to erroneous recognition of a tracking point due to various reasons, the resultant elastic modulus is a meaningless value. Hereinafter, this viewpoint will be described in detail.

Figure 6:
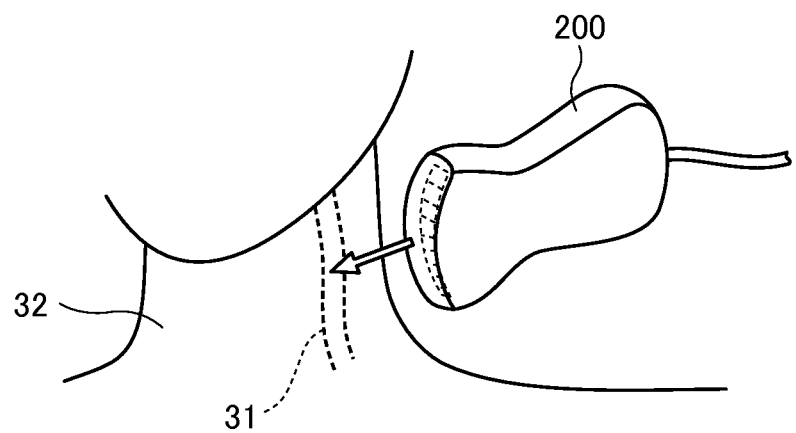
FIG. 6 is a schematic view showing a condition in which the elastic modulus of a carotid artery of a person is measured.

As a typical example, in this specification, a case where an elastic modulus is measured for a carotid artery will be described. When a carotid artery is taken as the target, there is a phenomenon in which the precision of an elastic modulus is considerably degraded in a specific case. FIG. 6 is a diagram showing a mode in which the elastic modulus of the carotid artery of a person is measured using the ultrasound diagnostic apparatus 100 of this embodiment. In this case, the carotid artery wall is observed while the ultrasound probe 200 abuts on a cervical region 32 of the subject along the carotid artery 31.

Since the depth of the carotid artery 31 is approximately 1 to 3 cm, a depth D necessary for the observation is about 3 cm. It is known that the average sound speed Vs in a human body is 1400 to 1600 m/s, in a carotid artery of a healthy person, the boundary between an intravascular cavity and a posterior vascular wall intima is displaced by about 0.5 mm in one heartbeat, and the displacement rate of the boundary in the depth direction is about 5 to 8 mm/s. For this reason, in order to calculate reliable distortion ϵ with satisfactory reproducibility, it is necessary to suppress measurement errors of tracking points set in the boundary and the surroundings to be equal to or smaller than 10% of 0.5 mm which is the amount of displacement of the carotid artery wall in one heartbeat, thereby tracking the tracking points with precision. Accordingly, when a carotid artery of a healthy person is observed, 0.05 mm÷5 m/s=0.01 s, and in order to acquire the displacement of 0.05 mm, it is necessary that a frame rate FR is equal to or higher than 100 l/s. In the case of a subject who has the fast motion of the vascular wall depending on the heartbeat due to a high blood pressure or the like, it is preferable that the frame rate be about 400 l/s. From these, in the ultrasound diagnostic apparatus 100, D=3, Vs=1400 m/s, and FR=400 l/s. It is assumed that the number of ultrasonic beam transmissions per frame is 58.

Figure 7A:
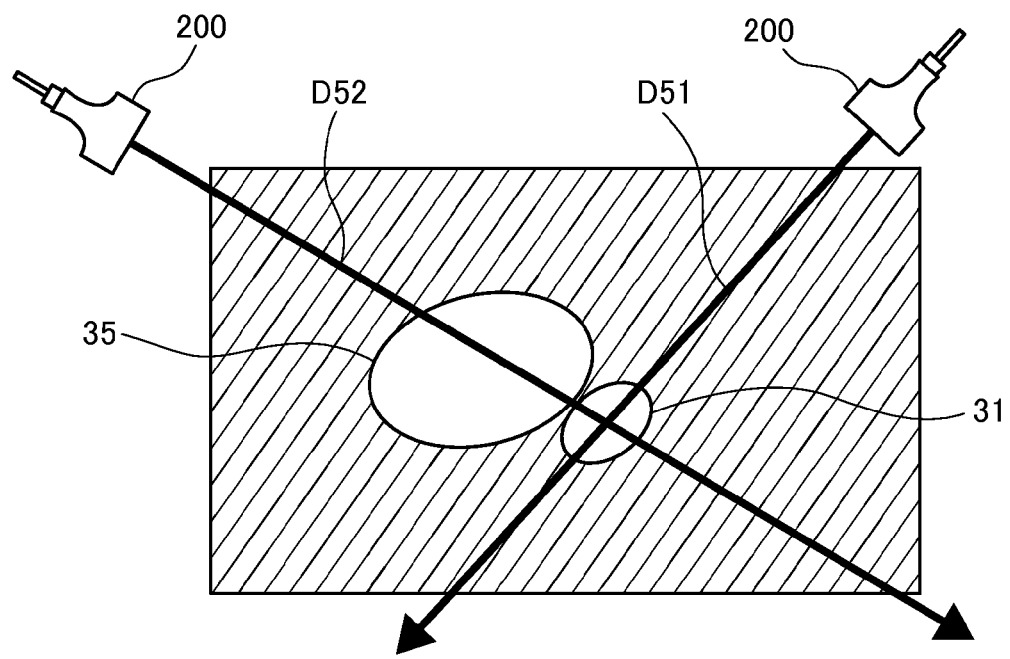
FIG. 7A is a schematic view illustrating a variation in an abutment angle of an ultrasound probe on a cervical region when viewed from a head region according to Embodiment 1 and including the cross section of the cervical region.
Figure 7B:
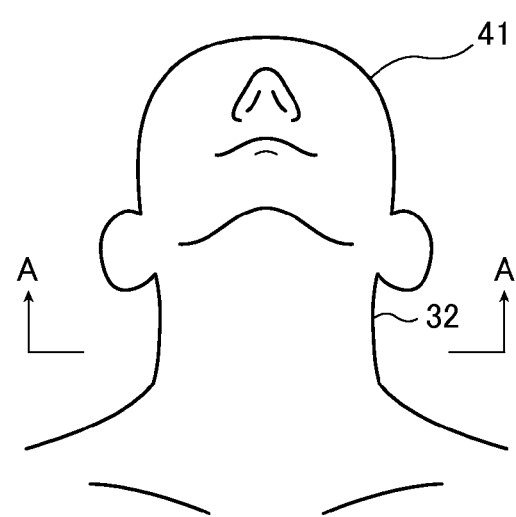
FIG. 7B is a schematic view of a head region and a cervical region of a person.

As shown in FIG. 6, although the ultrasound probe 200 abuts on the cervical region 32 along the carotid artery 31, from the detailed verification of the inventors, in general, there are broadly two patterns regarding from which direction of the cervical region 32 a physician or a technician (hereinafter, simply referred to as a technician) abuts the ultrasound probe 200 on the cervical region 32. FIG. 7A is a schematic view illustrating a variation in the abutment angle of the ultrasound probe 200 on the cervical region 32. FIG. 7A is a sectional view of the cervical region 32 taken along the line A-A of FIG. 7B when viewed from a head region 41. As shown in FIG. 7A, with regard to the direction in which the ultrasound probe 200 abuts on the cervical region 32, there are the following two methods. A first method is a method in which the ultrasound probe 200 abuts from a direction D51 and the carotid artery 31 is observed. This corresponds to a case where the ultrasound probe 200 abuts in front of the subject. A second method is a method in which the ultrasound probe 200 abuts from a direction D52, and with the jugular vein 35 as a window, the carotid artery 31 is observed beyond the window (through the jugular vein 35). At this time, an ultrasonic beam transmitted from the ultrasound probe 200 passes through the jugular vein 35 and then reaches the carotid artery 31. This way of abutment corresponds to a case where the ultrasound probe 200 abuts from the side of the subject.

One of the reasons for the use of the second method resides in that, since a vein is filled with blood, the ultrasonic beam is little reflected, and as shown in FIG. 7A, the jugular vein is close to the carotid artery. For this reason, it is possible to prevent a phenomenon (fogging phenomenon) in which an artifact from a tissue (jugular vein) through which the ultrasonic beam first passes is superimposed on an ultrasound image of a tissue (carotid artery) as a diagnostic target, and the intravascular cavity is blurred. That is, the reason is considered to be that, according to the second method, an image with comparatively satisfactory image quality is likely to be obtained.

Figure 8A:
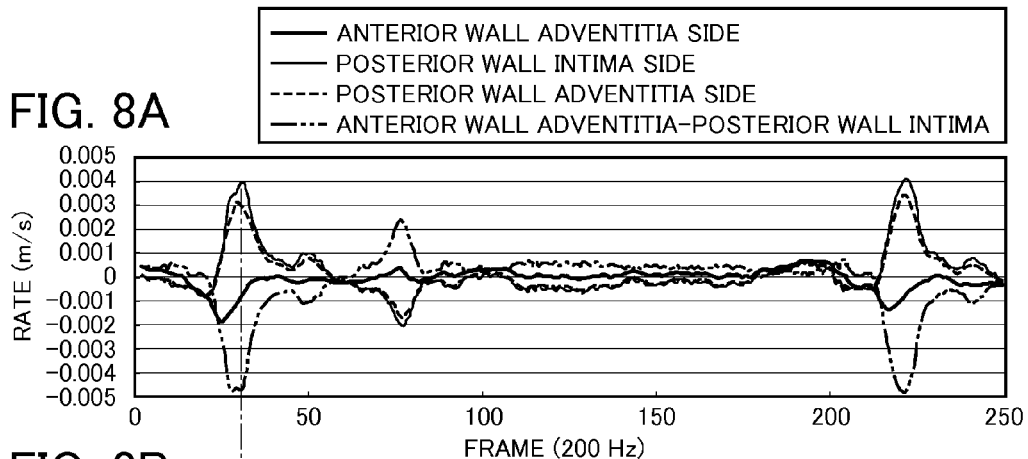
FIGS. 8A to 8C are graphs showing an example of time-varying waveforms of a change rate of the diameter of a vascular wall at each position, a blood vessel diameter, and a displacement of each tracking point of the vascular wall.
Figure 8B:
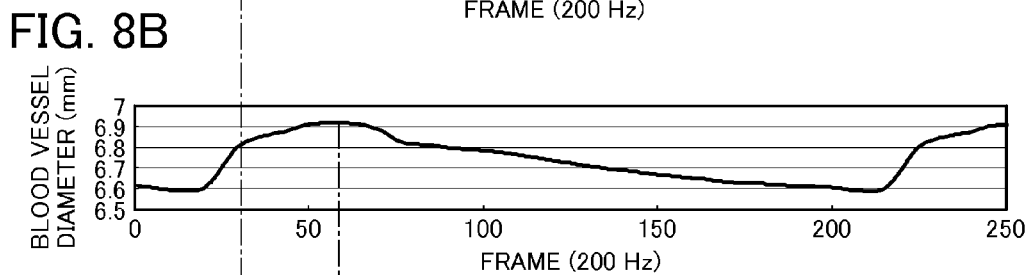
Figure 8C:
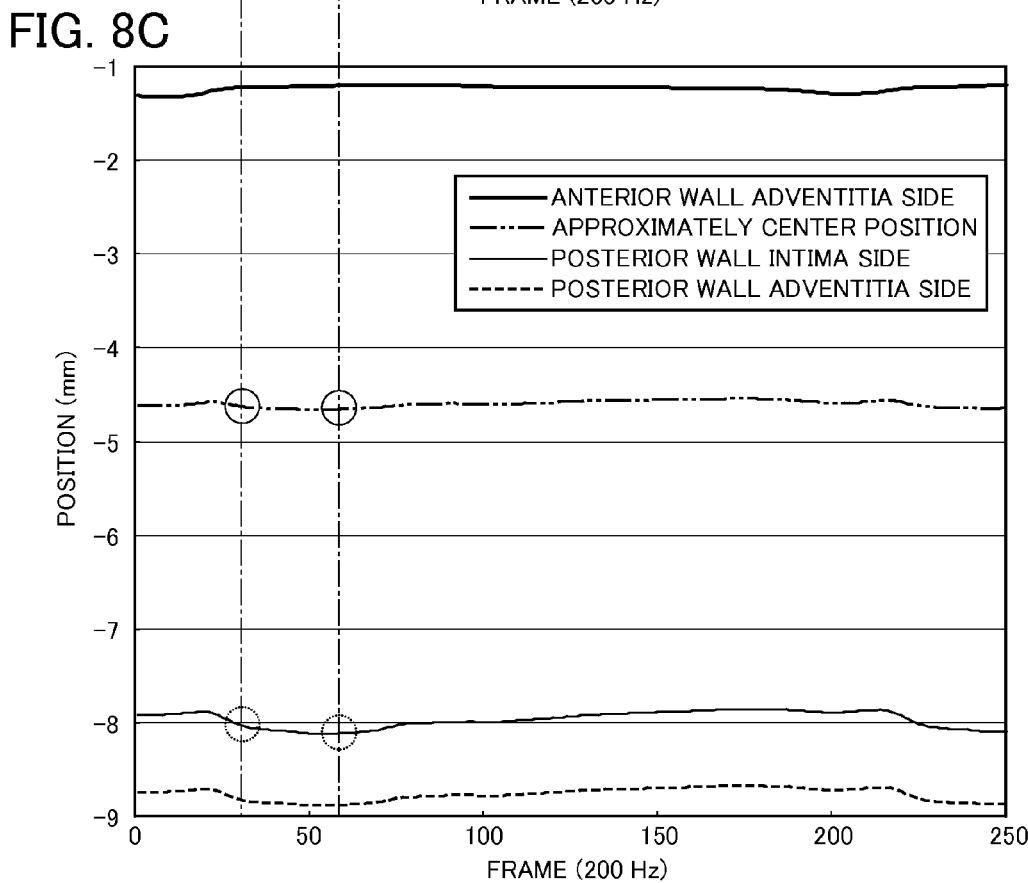

FIGS. 8A to 8C show an example of time-varying waveforms of indexes (hereinafter, collectively referred to as a vascular wall thickness) relating to the vascular wall with high reliability when tracking of the vascular wall is performed with satisfactory precision. In this example, the ultrasound probe 20C abuts in front of the subject, and measurement is performed.

Specifically, FIG. 8A is a diagram showing temporal changes in the change rate of the diameter of the vascular wall at respective positions (specifically, an anterior wall adventitia side, a posterior wall intima side, a posterior wall adventitia side, and an anterior wall adventitia-anterior wall intima). FIG. 8B is a diagram showing a temporal change in a blood vessel diameter (specifically, the distance between the anterior wall adventitia and the posterior wall intima). FIG. 8C is a diagram showing temporal changes in displacement at respective tracking points (specifically, a position on the anterior wall adventitia side, an approximately center position, a position on the posterior wall intima side, and a position on the posterior wall adventitia side) of the vascular wall.

As will be understood from FIG. 8A, when the time-varying waveform of the vascular wall thickness with high reliability is obtained when tracking of the vascular wall is performed with satisfactory precision, the waveform appears in a state of being substantially vertically symmetrical with respect to the line of the rate 0. For example, if the anterior wall adventitia and the posterior wall intima or the posterior wall adventitia of FIG. 8A are substantially symmetrical, reliability increases. For example, in FIG. 8C, if the anterior wall adventitia side and the posterior wall intima side or the posterior wall adventitia side are substantially symmetrical, reliability increases. That is, it can be expected that the elastic modulus of the blood vessel with high reliability is generally obtained from the time-varying waveform of the vascular wall thickness having a substantially vertically symmetrical shape.

In FIG. 8C, although a two-dot-chain line represents the displacement of the approximately center position, and specifically, represents the displacement of the middle point between the anterior wall adventitia side and the posterior wall intima side. With regard to an accurate center position, the anterior wall intima side and the posterior wall intima side may be used. In this case, the anterior wall adventitia side and the posterior wall intima side which are easily diagnosed in ultrasound diagnosis (that is, an ultrasonic echo is strong, and noise, such as fog from other locations, is small) are used. In the ultrasound diagnosis, as described above, for reliability determination, it is determined whether or not the anterior wall and the posterior wall are symmetrically in motion. Accordingly, since the posterior wall intima side and the posterior wall adventitia side have the same motion on a scale, called a diameter change, a displacement waveform becomes (anterior wall adventitia side-posterior wall intima side displacement)≈(anterior wall intima side-posterior wall intima side displacement)≈(anterior wall adventitia side-posterior wall adventitia side displacement). From above, in FIG. 8A, a temporal change in the change rate of the anterior wall adventitia-anterior wall intima indicated by a two-dot-chain line is obtained.

Figure 9A:
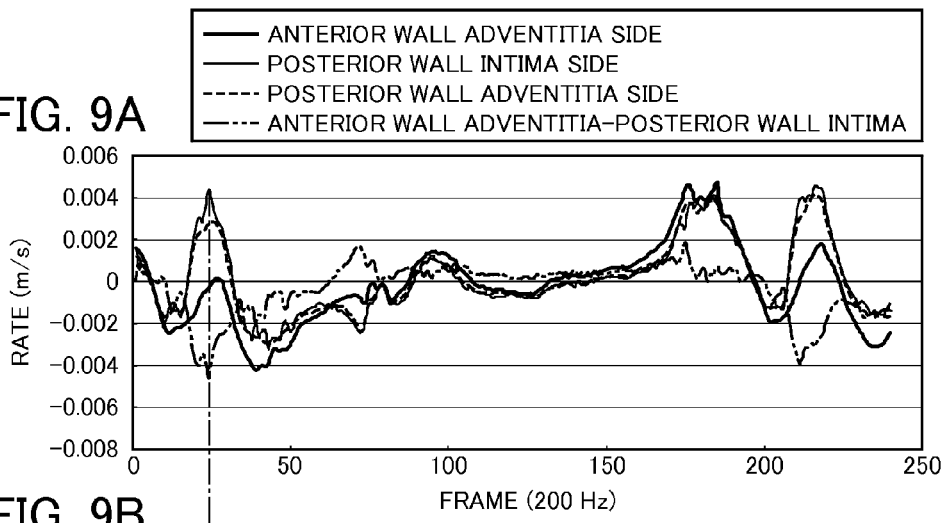
FIGS. 9A to 9C are graphs showing another example of time-varying waveforms of a change rate of the diameter of a vascular wall at each position, a blood vessel diameter, and a displacement of each tracking point of the vascular wall.
Figure 9B:
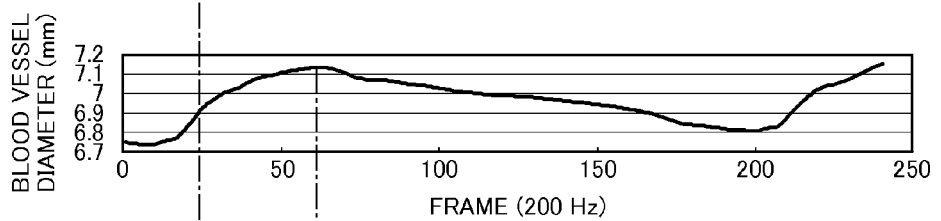
Figure 9C:
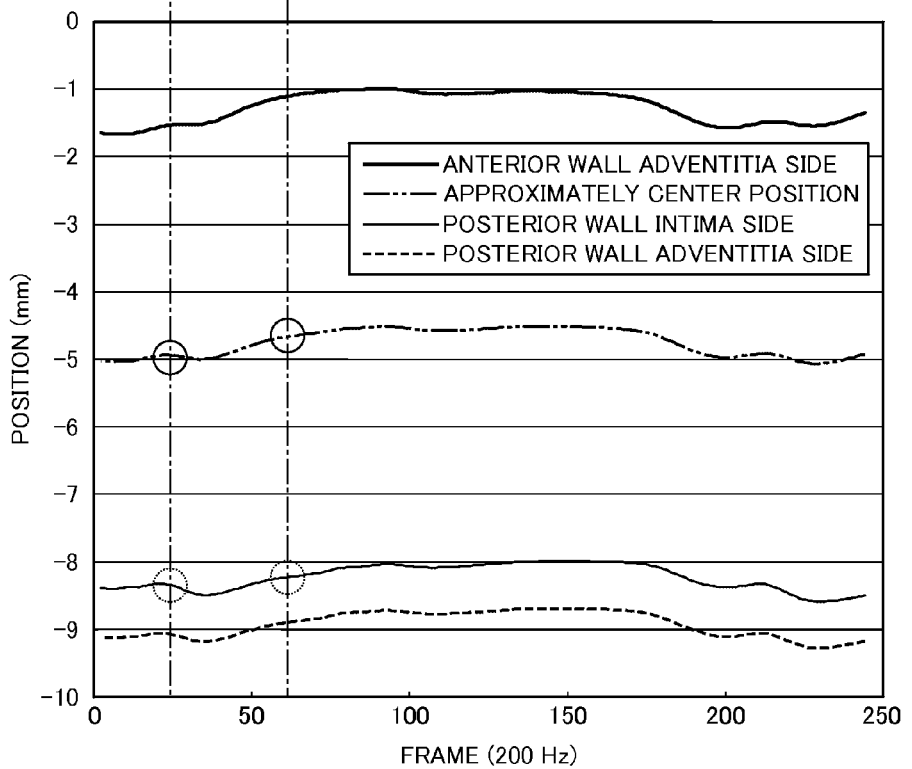

FIGS. 9A to 9C show an example of time-varying waveforms of indexes (vascular wall thickness) relating to the vascular wall with low reliability when the tracking precision of the vascular wall is not satisfactory. Similarly to FIGS. 8A to 8C, FIGS. 9A to 9C are diagrams showing temporal changes in the change rate of the diameter of the vascular wall at each position, a blood vessel diameter, and a displacement of the vascular wall at each tracking point. In this example, the ultrasound probe 200 abuts from the side of the subject, and measurement is performed. Unlike FIG. 8A, the waveform shown in FIG. 9A is vertically asymmetrical with respect to the line of the rate 0. This waveform is a waveform which is obtained when tracking of the vascular wall does not function normally. The elastic modulus of the blood vessel obtained at this time is generally predicted to have low reliability. In FIG. 9C, contrary to FIG. 8C, since the anterior wall adventitia side and the posterior wall intima side or the posterior wall adventitia side are not symmetrical, reliability is deteriorated.

The reason for which the reliability of the elastic modulus to be measured is low is considered. With regard to the measurement of the elastic modulus, it is necessary to track a minute displacement of the vascular wall in motion. However, if the position of the blood vessel itself is moved, a phenomenon is considered in which (1) the displacement of the blood vessel is shifted from the center axis of the ultrasonic beam in the elevation direction, (2) a fluctuation range itself increases and then an error when the minute displacement is tracked increases, (3) the hand of the technician is primarily shifted, and the abutment position of the ultrasound probe is shifted, or the like. From this fact, the inventors have thought that it is to be determined whether or not the position of the blood vessel itself is being largely moved so as to evaluate and determine reliability. Accordingly, the ultrasound diagnostic apparatus 100 of this embodiment obtains the center position of the blood vessel and acquires the temporal change in the center position of the blood vessel to determine the reliability of the measured elastic modulus of the blood vessel. Specifically, the ultrasound diagnostic apparatus 100 calculates the average of the positions of the anterior wall and the posterior wall of the blood vessel, and sets the average as the center position of the blood vessel. When higher precision is demanded, the average of the position of the anterior wall adventitia and the position of the posterior wall intima may be calculated and set as the center position of the blood vessel. That is, the middle of the position of the anterior wall adventitia and the position of the posterior wall intima may be set as the center position of the blood vessel.

FIG. 10 is a table which represents a blood vessel center displacement in one heartbeat, displacements from a minimum diameter timing to a maximum diameter timing of the posterior vascular wall and the blood vessel center, and the reliability of the elastic modulus when a time-varying waveform of a vascular wall thickness with high reliability is obtained and when a time-varying waveform of a vascular wall thickness with low reliability is obtained.

First, description will be provided as to a blood vessel center displacement in one heartbeat, displacements from a minimum diameter timing to a maximum diameter timing of the posterior vascular wall and the blood vessel center, and the reliability of the elastic modulus when measuring from two different directions of FIG. 10, that is, when measuring from "anterior (front)" in which a time-varying waveform of a vascular wall thickness with high reliability is obtained and when measuring with "a vein as a window" in which a time-varying waveform of a vascular wall thickness with low reliability is obtained.

In the case of a healthy person, generally, with regard to the reliability of the elastic modulus, it is predicted that the elastic modulus is equal to or smaller than 300 kPa. Accordingly, when the elastic modulus is equal to or smaller than 300 kPa, it is evaluated as "reliability: O", and when a value considerably distant from 300 kPa is used, it is evaluated as "reliability: x". As will be understood from this drawing, while, when measuring from the front (the cases of FIGS. 8A to 8C), the reliability of the elastic modulus is high, when measuring from the side with the jugular vein as a window (the cases of FIGS. 9A to 9C), the reliability of the elastic modulus is lacking.

Focusing on the amount of displacement of the blood vessel center position, it is understood that, when the amount of displacement of the center position of the blood vessel is near 0.1 mm (0.09 to 0.12), reliability is "O" and reliability is high. It is understood that, when the amount of displacement of the center position of the blood vessel is equal to or greater than 0.49 mm, reliability is "x" and reliability is low.

Focusing on the amount of displacement from the minimum diameter timing to the maximum diameter timing of the blood vessel center, it is understood that, when the amount of displacement from the minimum diameter timing to the maximum diameter timing of the blood vessel center has a slightly negative value (−0.07 mm to −0.03 mm), reliability is "O" and reliability is high. It is understood that, when the amount of displacement between both timings of the blood vessel center has a positive value (0.24 mm to 0.34 mm) equal to or greater than 0.24 mm, reliability is "x" and reliability is low. In this embodiment, when the amount of displacement between both timings of the blood vessel center is equal to or greater than 0.24 mm toward the anterior wall, it can be determined that the reliability of the elasticity index is low.

Accordingly, when the center position of the blood vessel is displaced by 0.24 mm or more toward the anterior wall, the ultrasound diagnostic apparatus 100 of this embodiment determines that the reliability of the elasticity index is low.

Figure 11A:
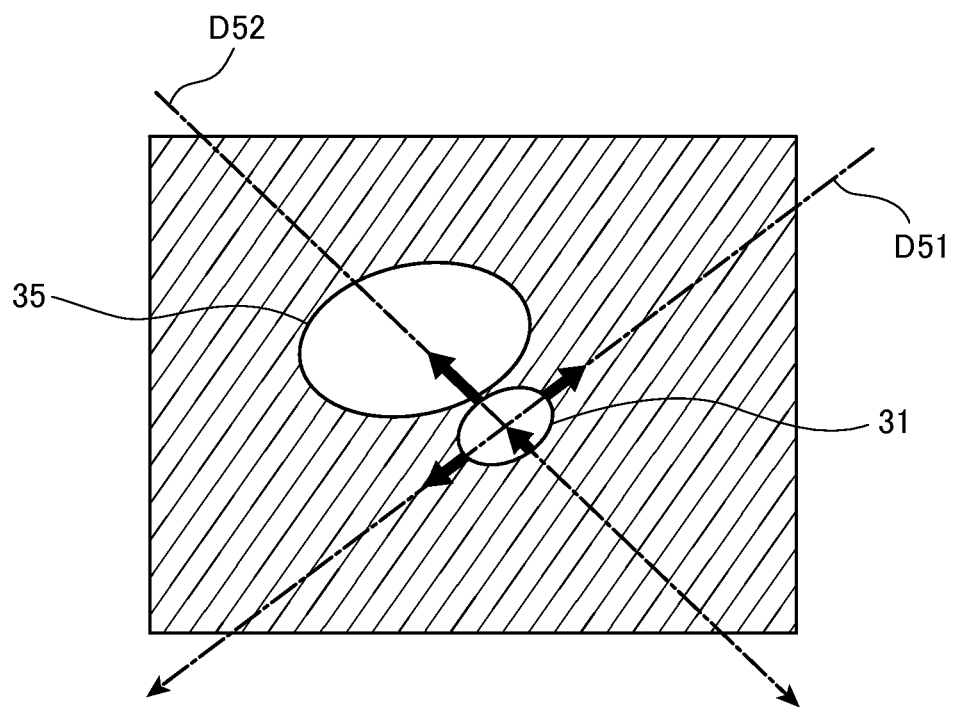
FIGS. 11A and 11B are schematic views illustrating a cause for deterioration in the reliability of an elastic modulus.
Figure 11B:
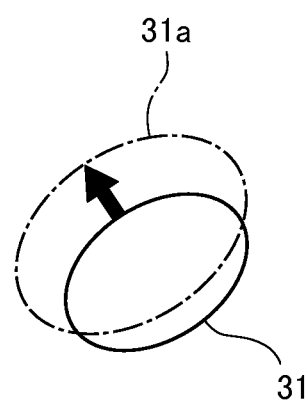

As described above, in particular, it is understood that, when a carotid artery is observed beyond a window of a jugular vein, the reliability of the elastic modulus is deteriorated. FIGS. 11A and 11B are schematic views illustrating a reason for deterioration in the reliability of the elastic modulus. From these drawings, it is possible to infer a mechanism which causes deterioration in the reliability of the elastic modulus. For example, there is a situation in which, in the direction D51, the carotid artery 31 is interposed between both tissues in the direction D51 and is difficult to move. Meanwhile, since the jugular vein 35 has pressure lower than surrounding tissues in the direction D52, there is a situation in which the carotid artery 31 is likely to expand toward the jugular vein 35. Accordingly, as shown in FIG. 11B, the carotid artery 31 expands while leaning to the jugular vein 35 (the contour of a carotid artery 31a after expansion is indicated by a broken line). In this case, it is considered that, since a state where (1) the displacement of the blood vessel is shifted from the center axis of the ultrasonic beam in the elevation direction, or (2) a fluctuation range itself increases and then an error when a minute displacement is tracked increases considerably appears, the reliability of the elastic modulus is deteriorated. As will be understood from FIG. 11A, the center of the carotid artery 31 moves in the direction D52, but moves little in the direction D51.

Although an example has been described in which, when the analysis of the mechanism for deterioration in reliability is in progress, the center position of the blood vessel is obtained and reliability is determined on the basis of the displacement in the above case, it is understood that reliability can be determined by observing the motion of the posterior vascular wall having a specific displacement direction as in the case where the carotid artery is observed in the direction D52 beyond the window of the jugular vein. That is, the inventors have found that, focusing on only the posterior vascular wall from among the layers constituting the blood vessel, the posterior vascular wall is directly tracked, making it possible to determine the reliability of the elastic modulus.

Figure 12:
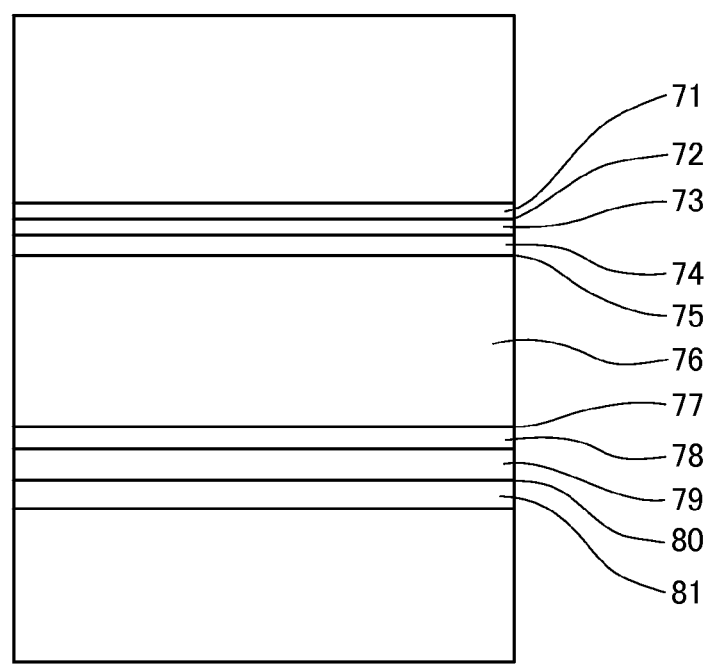
FIG. 12 is a sectional view schematically showing the layered structure of a carotid artery.

FIG. 12 is a sectional view schematically showing the layered structure of the carotid artery. A detailed sectional view is shown in which a posterior wall intima 78, a posterior wall media 79, and a posterior wall adventitia 81 are shown as the posterior vascular wall. In this embodiment, a "posterior wall vascular cavity-intima boundary 77" or "posterior wall media-adventitia boundary 80" having high following performance through tracking out of the posterior vascular wall as a tracking target is used. In particular, since the vascular cavity has a low signal level in image data, tracking is likely to fail. Accordingly, the "posterior wall vascular cavity-intima boundary 77" or "posterior wall media-adventitia boundary 80" whose line clearly appears on an M-mode image is preferably used. Accordingly, a measurement time is reduced, thereby reducing the load imposed on a physician or a subject.

FIG. 12 shows an anterior wall adventitia 71, an anterior wall media 73, and an anterior wall intima 74 as the anterior vascular wall, and also shows an anterior wall adventitia-media boundary 72, an anterior wall intima-vascular cavity boundary 75, and a vascular cavity 76.

The inventors have further reached a novel concept. In normal tracking, it is assumed that the position of the blood vessel is not changed along with the heartbeat and the blood vessel diameter simply expands and contracts. At this time, the vascular wall simply expands and contracts along with the heartbeat with the blood vessel center as a symmetric axis. That is, the anterior vascular wall and the posterior vascular wall are displaced in opposing directions toward the outside of the blood vessel. However, as described above, when obtaining an image of the carotid artery with the jugular vein as a window, the entire blood vessel is shifted (moved) toward the jugular vein with the heartbeat. At this time, while the anterior vascular wall out of the vascular wall is displaced in the same direction as the normal tracking, in many cases, the posterior vascular wall is displaced in the same direction as in the anterior vascular wall, that is, toward the anterior wall, instead of being displaced toward the outside of the blood vessel. Accordingly, the inventors have focused on the displacement direction of the posterior vascular wall and have conceived that the reliability of the elastic modulus can be determined by the direction.

FIGS. 13A, 13B, and 13C are graphs showing a displacement (displacement direction and amount of displacement) of each site (vascular wall position: tracking point) in one heartbeat when measuring from different directions (from anterior and from the side with a vein as a window) and measuring from the side with the jugular vein as a window in a state where the ultrasound probe is pushed and abutted on the subject.

First, FIGS. 13A and 13B corresponding to the case where measurement is performed from two different directions of "anterior" and "side with vein as window" in the table of FIG. 10 will be subsequently described.

As will be understood from these drawings, the displacement direction has a characteristic, and in the case of FIG. 13B in which reliability is deteriorated, when the displacement direction, specifically, the displacement of the posterior wall is toward the anterior wall, reliability is deteriorated. Although in FIGS. 8A to 8C or FIGS. 9A to 9C, the reliability of the elastic modulus can be predicted on the basis of the time-varying waveform of the vascular wall thickness to some extent, in FIGS. 13A and 13B, it is understood that the reliability of the elastic modulus can be determined from the displacement direction of the vascular wall.

When measurement is performed from two different directions in the table of FIG. 10, it can be said that the table is used to determine reliability from the displacement direction of the vascular wall. Description will be provided as to the displacement from the minimum diameter timing to the maximum diameter timing of the posterior vascular wall in FIG. 10. As will be understood from the table, when the amount of displacement between the minimum and maximum diameter timings of the posterior vascular wall is a negative value equal to or smaller than −0.14 mm (−0.19 mm to −0.14 mm), it is understood that reliability is "O" and reliability is high. That is, when the posterior vascular wall is displaced toward the outside of the blood vessel in the heart contraction phase, it can be evaluated and determined that the reliability of the elasticity index is high.

On the other hand, when the amount of displacement between both timings of the posterior vascular wall is a positive value equal to or greater than 0.11 mm, it is understood that reliability is "x" and reliability is lacking. Accordingly, when the posterior vascular wall is displayed by 0.11 mm or more toward the anterior wall, the ultrasound diagnostic apparatus 100 of this embodiment determines that the reliability of the elasticity index is low.

Through additional studies by the inventors, it is understood that there is a measurement method which, even when measurement is performed from the side with the jugular vein as a window, can suppress the amount of displacement of the center position of the blood vessel, thereby acquiring a reliable elastic modulus.

FIG. 13C is a graph showing a displacement (displacement direction and amount of displacement) of each site (vascular wall position: tracking point) of the blood vessel in one heartbeat when measuring from the side with the jugular vein as a window. Meanwhile, the ultrasound probe may be pushed and abutted on the subject to perform measurement. In this way, external pressure is applied to the jugular vein to increase the pressure in the jugular vein and therefore it is considered that the carotid artery is difficult to move toward the jugular vein, and the amount of displacement of the blood vessel is suppressed, thereby acquiring a reliable elastic modulus.

The table of "press with vein as window" of FIG. 10 is the table which shows the reliability of the elastic modulus in the case of FIG. 13C, that is, the case where the ultrasound probe is pushed and abutted on the subject and measurement is performed from the side with the jugular vein as a window.

As will be understood from the table, focusing on the amount of displacement of the blood vessel center position, it is understood that the amount of displacement of the center position of the blood vessel is slightly greater than when measuring from the front (anterior) and significantly smaller than when measuring from the side with the jugular vein as a window. In this case, the displacement toward the anterior wall is 0.12 mm to 0.21 mm, that is, is smaller than 0.3 mm, reliability is "O", and reliability is high.

Focusing on the amount of displacement from the minimum diameter timing to the maximum diameter timing of the blood vessel center, it is understood that the amount of displacement is greater than when measuring from the front (anterior) and is significantly smaller than when measuring from the side with the jugular vein as a window. The displacement toward the anterior wall is −0.01 mm to +0.08 mm, that is, is smaller than 0.01 mm, reliability is "O", and reliability is high.

Focusing on the displacement direction from the amount of displacement from the minimum diameter timing to the maximum diameter timing of the posterior vascular wall, it is understood that, similarly to the case where measurement is performed from the front (anterior), the displacement direction of the posterior vascular wall is the displacement toward the posterior vascular wall, not the displacement of the posterior vascular wall toward the anterior wall as seen when measurement is performed from the side with the jugular vein as a window. In this case, reliability is "O" and reliability is high.

As described above, even when measurement is performed from the side with the jugular vein as a window, it is understood that, when the ultrasound probe is pushed and abutted on the subject and measurement is performed from the side with the jugular vein as a window, a reliable elastic modulus is obtained.

According to the invention, even in a system in which the measurement result differs depending on the technique of the technician or the like, it is possible to give an objective index regarding whether or not the measurement may be continued.

As described above, according to the ultrasound diagnostic apparatus of the invention, in the ultrasound diagnostic apparatus which calculates the thickness change waveform of the vascular wall or the like based on a heart stroke, and calculates an elasticity index or an elastic image, the displacement of the vascular wall or the blood vessel center position is calculated and displayed, thereby giving a warning relating to the reliability of the elasticity of the blood vessel. As described above, the lowering in the measurement precision of the elastic modulus of the blood vessel is caused by the direction in which the measurement technician abuts the ultrasound probe on the human body, or the like, and if the probability that the measurement precision is lowered can be provided to the measurement technician, the measurement technician can correct the abutment direction of the ultrasound probe, the degree of compression, or the like, thereby avoiding the lowering of the measurement precision.

In the above-described configuration, in the ultrasound diagnostic apparatus which calculates the thickness change waveform of the vascular wall or the like based on a heart stroke, and calculates an elasticity index or an elastic image, the amount of displacement of the vascular wall or the blood vessel center position is calculated and displayed, thereby giving a warning relating to the reliability of the elasticity of the blood vessel.

The above-described embodiment of the invention is merely illustrative of the invention, and is not intended to limit the configuration of the invention. The ultrasound diagnostic apparatus or the like according to the invention is not limited to the above-described embodiment, and various changes may be made without departing from the object of the invention.

For example, although in this specification, a case has been described where the reliability of the vascular elastic modulus of the carotid artery is determined, intrinsically, the invention can be applied to a case where a local point which pulsates due to the heartbeat is tracked to measure an elasticity index, such as an elastic modulus. That is, the target is not limited to the carotid artery, and may be abdominal aorta, iliac artery or the like.

A local point may not pulsate. A system may be used in which an external force is applied to move a tracking point, whereby an elastic modulus can be measured on the basis of the movement direction and the displacement.

Although in the foregoing embodiment, a case has been described where the elastic modulus is used as the elasticity index of the blood vessel, distortion of the blood vessel in the radial direction may be used as the elasticity index of the blood vessel.

Although in the foregoing embodiment, the configuration is implemented by a central processing unit (CPU) and software which causes the CPU to perform various processes, these may be implemented by hardware, such as digital circuits or analog circuits. Software is stored in an internal memory (not shown).

The algorithm of the method of evaluating or determining elasticity index reliability of the blood vessel according to the invention is described in a programming language, and compiled as necessary. The program for evaluating or determining elasticity index reliability of the blood vessel is stored in a memory (storage medium) and executed by an information processing unit of another device. Therefore, it is possible to realize the same functions as the ultrasound diagnostic apparatus according to the invention.

That is, the method of evaluating or determining elasticity index reliability of the blood vessel according to the invention can be processed on a computer by executing the program.

For example, the program for evaluating or determining elasticity index reliability of the blood vessel according to the invention has a procedure for causing the computer, specifically the CPU, to execute the respective steps of the method of evaluating or determining elasticity index reliability of the blood vessel. The program having this procedure may be constituted by one or a plurality of program modules.

The program for evaluating or determining elasticity index reliability of the blood vessel having the procedure to be executed by the computer may be stored in a memory (storage device) of the computer or a server, or may be stored in a storage medium. At the time of execution, the program is read out from the memory or the storage medium by the computer (CPU) or another computer and executed. Therefore, the invention may be implemented as a computer readable memory or storage medium which stores the program for evaluating or determining elasticity index reliability of the blood vessel for causing the computer to execute the method of evaluating or determining elasticity index reliability of the blood vessel.

The ultrasound diagnostic apparatus, the method of evaluating or determining elasticity index reliability, and the program for evaluating or determining elasticity index reliability according to the embodiments of the invention may be used for the purposes of, for example, an ultrasound diagnostic apparatus which is loaded on a cart and moved to each room in a hospital, a lightweight and portable ultrasound diagnostic apparatus which is used at patient's home, a measurement system which measures only an elasticity index of a blood vessel using an ultrasonic wave, and the like.

What is claimed is:

1. An ultrasound diagnostic apparatus which is configured to determine reliability of an elasticity index of a blood vessel of a subject by transmitting ultrasonic beams toward the blood vessel of the subject and receiving ultrasonic echoes reflected by the blood vessel of the subject using an ultrasound probe pushed and abutted on an outer surface of the subject, comprising:
    a controller which controls transmission and reception of the ultrasonic beams;
    a tracking unit configured to track displacements in a transmission direction of a plurality of points of the blood vessel in the transmission direction of the ultrasonic beams;
    a calculator which calculates the elasticity index of the blood vessel based on the tracking result of the tracking unit;
    an acquisition unit configured to acquire the direction of a displacement and/or the amount of the displacement in the transmission direction of one or more specific points being on a posterior vascular wall of the blood vessel among the plurality of points; and
    a determination unit configured to determine the reliability of the elasticity index based on the direction of the displacement and/or the amount of displacement of the one or more specific points acquired by the acquisition unit,
    wherein, when the posterior vascular wall is displaced toward outside of the blood vessel in a heart contraction phase, the determination unit is configured to determine that the reliability of the elasticity index is high based on the direction of the displacement of the one or more specific points being on the posterior vascular wall.

2. The ultrasound diagnostic apparatus according to claim 1,
    wherein, when the posterior vascular wall is displaced toward an anterior vascular wall by equal to or greater than 0.11 mm during a period in which the blood vessel increases from a minimum diameter to a maximum diameter, the determination unit is configured to determine that the reliability of the elasticity index is low based on the direction of the displacement and the amount of displacement of the one or more specific points being on the posterior vascular wall.

3. The ultrasound diagnostic apparatus according to claim 1,
    wherein the acquisition unit further is configured to acquire the direction of the displacement and the amount of displacement in the transmission direction of one or more specific points being on a posterior and an anterior vascular wall of the blood vessel among the plurality of points, and
    the determination unit further is configured to determine the direction of the displacement and the amount of the displacement of a center position of the blood vessel from the acquired direction of the displacement and the acquired amount of the displacement of both of the one or more specific points on the anterior vascular wall and the posterior vascular wall by the acquisition unit, and then the reliability of the elasticity index based on the determined direction of the displacement and the determined amount of the displacement of the center position of the blood vessel.

4. The ultrasound diagnostic apparatus according to claim 3,
    wherein, when the center position of the blood vessel is displaced toward the anterior wall by equal to or greater than 0.24 mm during a period in which the blood vessel increases from a minimum diameter to a maximum diameter, the determination unit is configured to determine that the reliability of the elasticity index is low.

5. The ultrasound diagnostic apparatus according to claim 3,
    wherein, when the center position of the blood vessel is displaced toward the anterior wall in one heartbeat is equal to or greater than 0.49 mm, the determination unit is configured to determine that the reliability of the elasticity index is low.

6. The ultrasound diagnostic apparatus according to claim 1, further comprising:
    a warning unit configured to give a warning when the determination unit determines that the reliability of the elasticity index is low.

7. The ultrasound diagnostic apparatus according to claim 1,
    wherein the blood vessel is a carotid artery of a human body.

8. A method of determining elasticity index reliability which determines reliability of an elasticity index of a blood vessel of a subject by transmitting ultrasonic beams toward the blood vessel of the subject and receiving ultrasonic echoes reflected by the blood vessel of the subject using an ultrasound probe pushed and abutted on an outer surface of the subject, the method comprising:
    a control step of controlling transmission and reception of the ultrasonic beams;
    a tracking step of tracking displacements in a transmission direction of a plurality of points of the blood vessel in the transmission direction of the ultrasonic beams;

a calculation step of calculating the elasticity index of the blood vessel based on the tracking result in the tracking step;

an acquisition step of acquiring the direction of a displacement and/or the amount of displacement in the transmission direction of one or more specific points being on a posterior vascular wall of the blood vessel among the plurality of points; and a determination step of determining the reliability of the elasticity index based on the direction of the displacement and/or the amount of displacement of the one or more specific points acquired in the acquisition step, wherein, when the posterior vascular wall is displaced toward outside of the blood vessel in a heart contraction phase, the reliability of the elasticity index is determined as being high based on the direction of the displacement of the one or more specific points being on the posterior vascular wall in the determination step.

9. A non-transitory computer readable storage medium with a program for determining elasticity index reliability stored therein, the program causing a computer to execute the control step, the tracking step, the calculation step, the acquisition step, and the determination step of the method of determining elasticity index reliability according to claim 8.

* * * * *